US00RE48649E

(19) United States
(12) Reissued Patent
Siess

(10) Patent Number: US RE48,649 E
(45) Date of Reissued Patent: Jul. 20, 2021

(54) INTRAVASCULAR ROTARY BLOOD PUMP

(71) Applicant: ABIOMED EUROPE GMBH, Aachen (DE)

(72) Inventor: Thorsten Siess, Aachen (DE)

(73) Assignee: Abiomed Europe GmbH, Aachen (DE)

(21) Appl. No.: 16/169,720

(22) Filed: Oct. 24, 2018

Related U.S. Patent Documents

Reissue of:
(64) Patent No.: 9,474,840
Issued: Oct. 25, 2016
Appl. No.: 14/396,700
PCT Filed: Apr. 26, 2013
PCT No.: PCT/EP2013/058715
§ 371 (c)(1),
(2) Date: Oct. 23, 2014
PCT Pub. No.: WO2013/160443
PCT Pub. Date: Oct. 31, 2013

(30) Foreign Application Priority Data

Apr. 27, 2012 (DE) ..... 10 2012 207 053

(51) Int. Cl.
*A61M 1/12* (2006.01)
*A61B 5/0215* (2006.01)
(Continued)

(52) U.S. Cl.
CPC ..... *A61M 60/135* (2021.01); *A61B 5/0036* (2018.08); *A61B 5/02154* (2013.01);
(Continued)

(58) Field of Classification Search
CPC ... A61B 5/02154; A61B 5/4836; A61B 5/686; G01L 9/0079; A61M 1/125;
(Continued)

(56) References Cited

U.S. PATENT DOCUMENTS 3,643,653 A * 2/1972 Takahashi ..... A61B 1/00165 600/129
4,945,230 A 7/1990 Saaski et al.
(Continued)

FOREIGN PATENT DOCUMENTS

CA 2576978 A1 3/2006
CA 2591787 A1 6/2006
(Continued)

OTHER PUBLICATIONS

U.S. Appl. No. 60/637,755, filed Dec. 22, 2004 (10 pages).
(Continued)

*Primary Examiner* — Cary E Wehner
(74) *Attorney, Agent, or Firm* — Botos Churchill IP Law

(57) ABSTRACT

An intravascular rotary blood pump possesses a catheter (10), a pumping device (50) disposed distally of the catheter and having at its distal end a flexible flow cannula (53) through which blood is either sucked or discharged by the pumping device (50) during operation of the blood pump, and at least one pressure sensor (27, 28A, 30) having at least one optical fiber (28A) which is laid along the flow cannula (53). The optical fiber (28A) and, where applicable, a sliding tube (27) in which the optical fiber (28A) is laid extend along a neutral fiber of the flow cannula (53).

27 Claims, 4 Drawing Sheets

(Amended)

Figure 1:
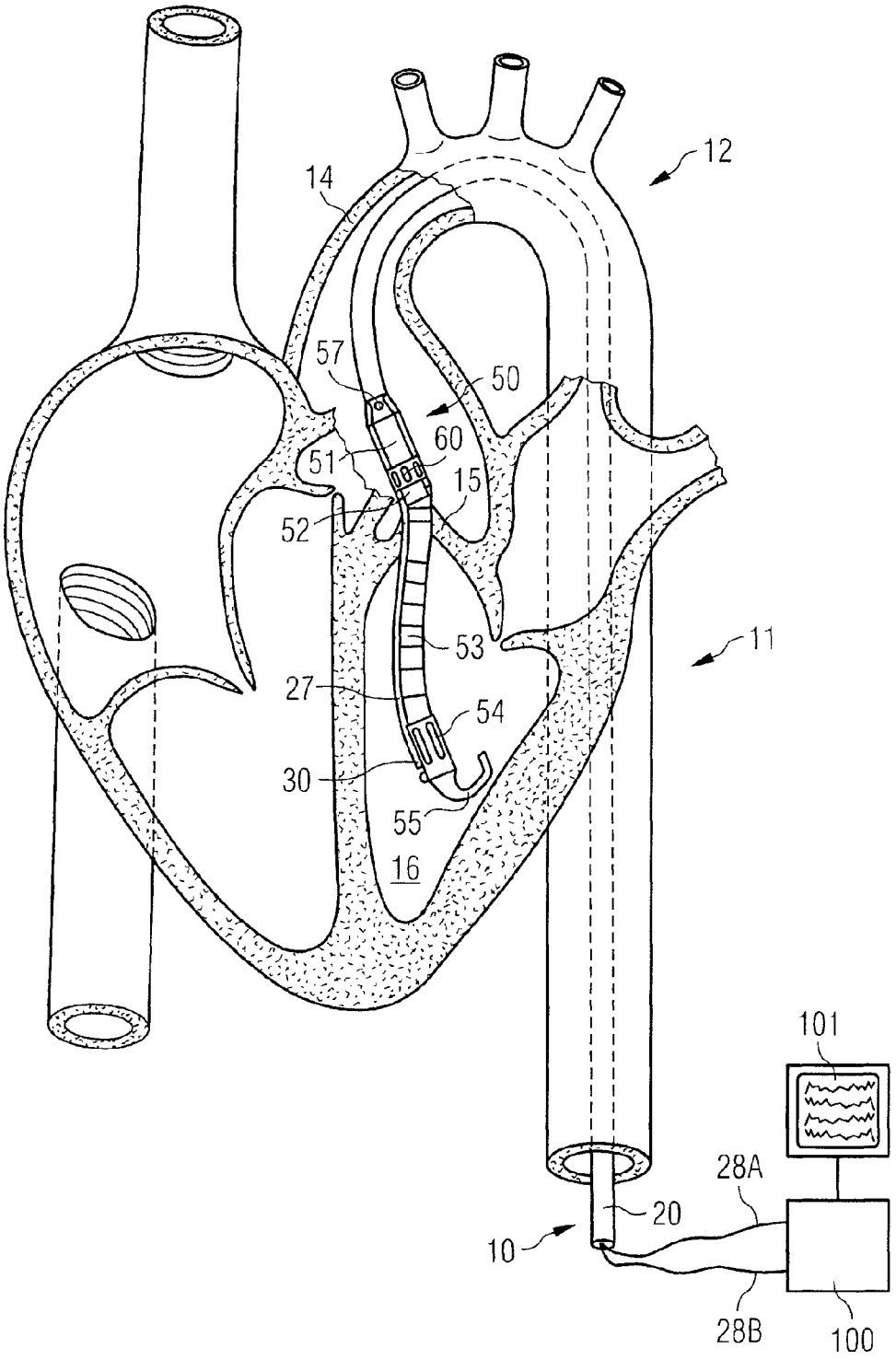

(51) Int. Cl.

| | |
|---|---|
| ***A61M 60/135*** | (2021.01) |
| ***A61B 5/00*** | (2006.01) |
| ***A61M 60/857*** | (2021.01) |
| ***G01L 9/00*** | (2006.01) |
| *A61M 60/148* | (2021.01) |
| *A61M 60/50* | (2021.01) |
| *A61M 60/40* | (2021.01) |
| *A61M 60/205* | (2021.01) |

(52) U.S. Cl.
CPC ..... *A61B 5/4836* (2013.01); *A61B 5/686* (2013.01); *A61M 60/857* (2021.01); *G01L 9/0079* (2013.01); *A61M 60/148* (2021.01); *A61M 60/205* (2021.01); *A61M 60/40* (2021.01); *A61M 60/50* (2021.01); *A61M 2205/0227* (2013.01); *A61M 2205/0238* (2013.01); *A61M 2205/0266* (2013.01); *A61M 2205/04* (2013.01); *A61M 2205/3303* (2013.01); *A61M 2205/3306* (2013.01); *A61M 2205/3331* (2013.01); *A61M 2205/3334* (2013.01); *A61M 2205/3344* (2013.01); *A61M 2205/3351* (2013.01); *A61M 2210/125* (2013.01); *A61M 2230/30* (2013.01)

(58) Field of Classification Search
CPC ..... A61M 1/1008; A61M 1/122; A61M 2205/3306; A61M 2205/3331; A61M 2205/3351; A61M 2205/0238; A61M 2205/04; A61M 2205/0266; A61M 2205/0227; A61M 1/1086; A61M 2230/30; A61M 2210/125; A61M 2205/3344; A61M 2205/3303; A61M 2205/3334; A61M 1/1029; A61M 1/101
USPC ..... 600/505, 139, 16, 17; 604/151, 524
See application file for complete search history.

(56) References Cited

U.S. PATENT DOCUMENTS

| | | | | |
|---|---|---|---|---|
| 5,645,531 | A * | 7/1997 | Thompson | A61M 1/3621 128/DIG. 3 |
| 5,911,685 | A | 6/1999 | Siess et al. | |
| 5,964,694 | A | 10/1999 | Siess et al. | |
| 6,007,478 | A * | 12/1999 | Siess | A61M 25/0053 600/16 |
| 6,176,822 | B1 | 1/2001 | Nix et al. | |
| 6,295,877 | B1 | 10/2001 | Aboul-Hosn et al. | |
| 6,398,738 | B1 | 6/2002 | Millar | |
| 6,733,459 | B1 | 5/2004 | Atsumi | |
| 7,022,100 | B1 | 4/2006 | Aboul-Hosn et al. | |
| 7,259,862 | B2 | 8/2007 | Duplain | |
| 7,689,071 | B2 | 3/2010 | Belleville et al. | |
| 8,752,435 | B2 | 6/2014 | Belleville et al. | |
| 2001/0051030 | A1 | 12/2001 | Hofner | |
| 2003/0187322 | A1 | 10/2003 | Siess | |
| 2004/0022640 | A1 | 2/2004 | Siess et al. | |
| 2009/0074367 | A1 | 3/2009 | Shinoski et al. | |
| 2010/0241008 | A1 | 9/2010 | Belleville et al. | |
| 2012/0227505 | A1 | 9/2012 | Belleville et al. | |
| 2013/0030363 | A1 * | 1/2013 | Wong | A61B 5/065 604/95.04 |

FOREIGN PATENT DOCUMENTS

| | | | |
|---|---|---|---|
| CA | 2819564 | A1 | 9/2012 |
| CN | 100451694 | | 1/2009 |
| DE | 3539638 | C1 | 5/1987 |
| DE | 3817915 | A1 | 11/1989 |
| EP | 1803004 | A1 | 7/2007 |
| EP | 1834164 | A1 | 9/2007 |
| EP | 1911484 | | 4/2008 |
| EP | 1911484 | A2 | 4/2008 |
| EP | 2638375 | A1 | 9/2013 |
| JP | 4994244 | B2 | 8/2012 |
| JP | 5264172 | B2 | 8/2013 |
| WO | 00/037139 | A1 | 6/2000 |
| WO | WO 00/037139 | | 6/2000 |
| WO | 01/074419 | A1 | 10/2001 |
| WO | WO 01/074419 | | 10/2001 |
| WO | 02/047751 | A2 | 6/2002 |
| WO | WO 02/047751 | | 6/2002 |
| WO | WO2006/032128 | | 3/2006 |
| WO | WO00/6066393 | | 6/2006 |
| WO | 2011/039091 | A1 | 4/2011 |
| WO | WO 2011/039091 | | 4/2011 |
| WO | WO2013/160407 | | 10/2013 |
| WO | WO2015/160943 | | 10/2015 |
| WO | WO2017/137578 | | 8/2017 |

OTHER PUBLICATIONS

International Search Report (PCT/US2017/036117) dated Jan. 9, 2017 (3 pages).
International Search Report (PCTEP2017/053033) dated Apr. 24, 2017.

* cited by examiner

FIG 2 (Amended)
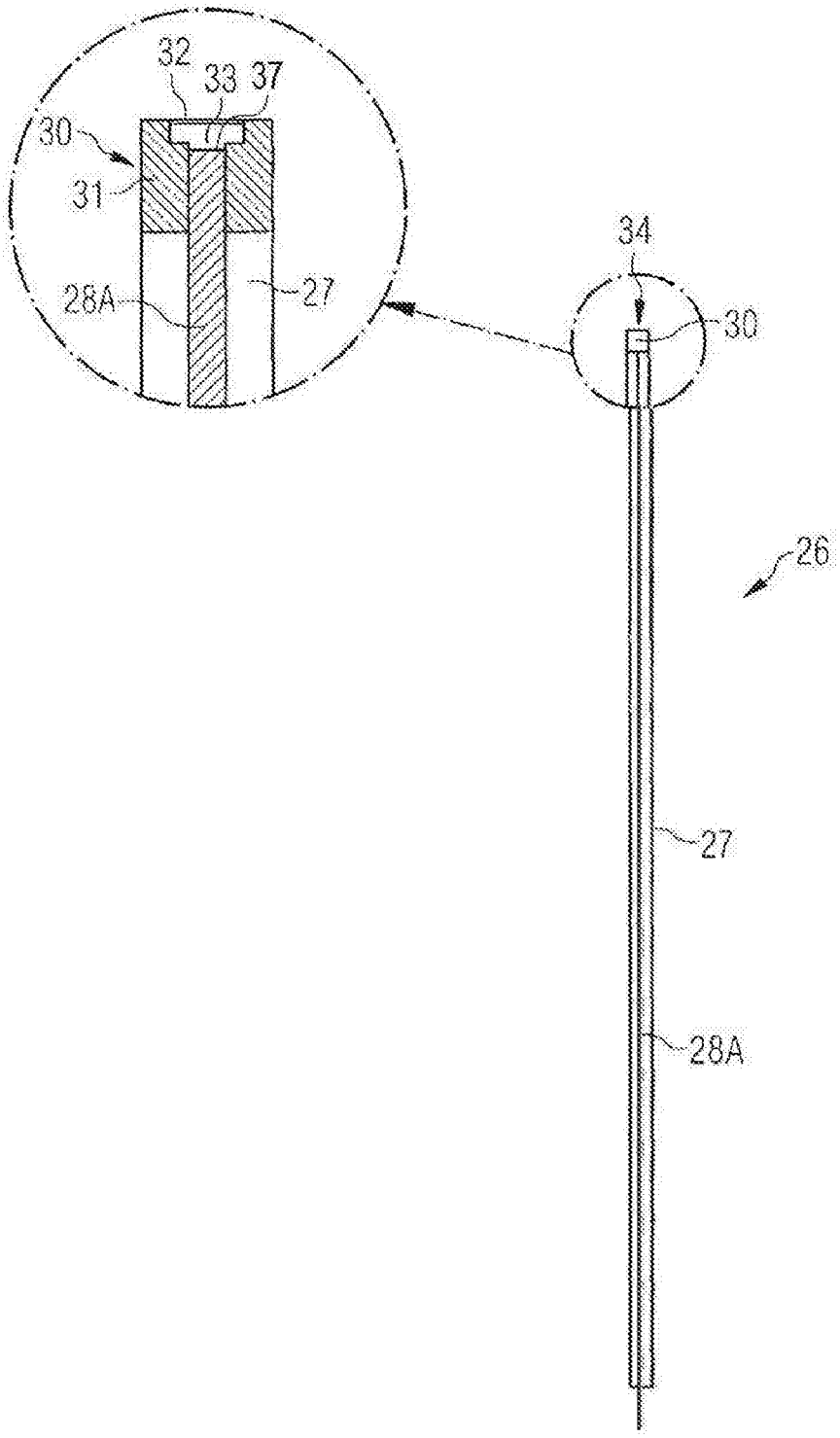

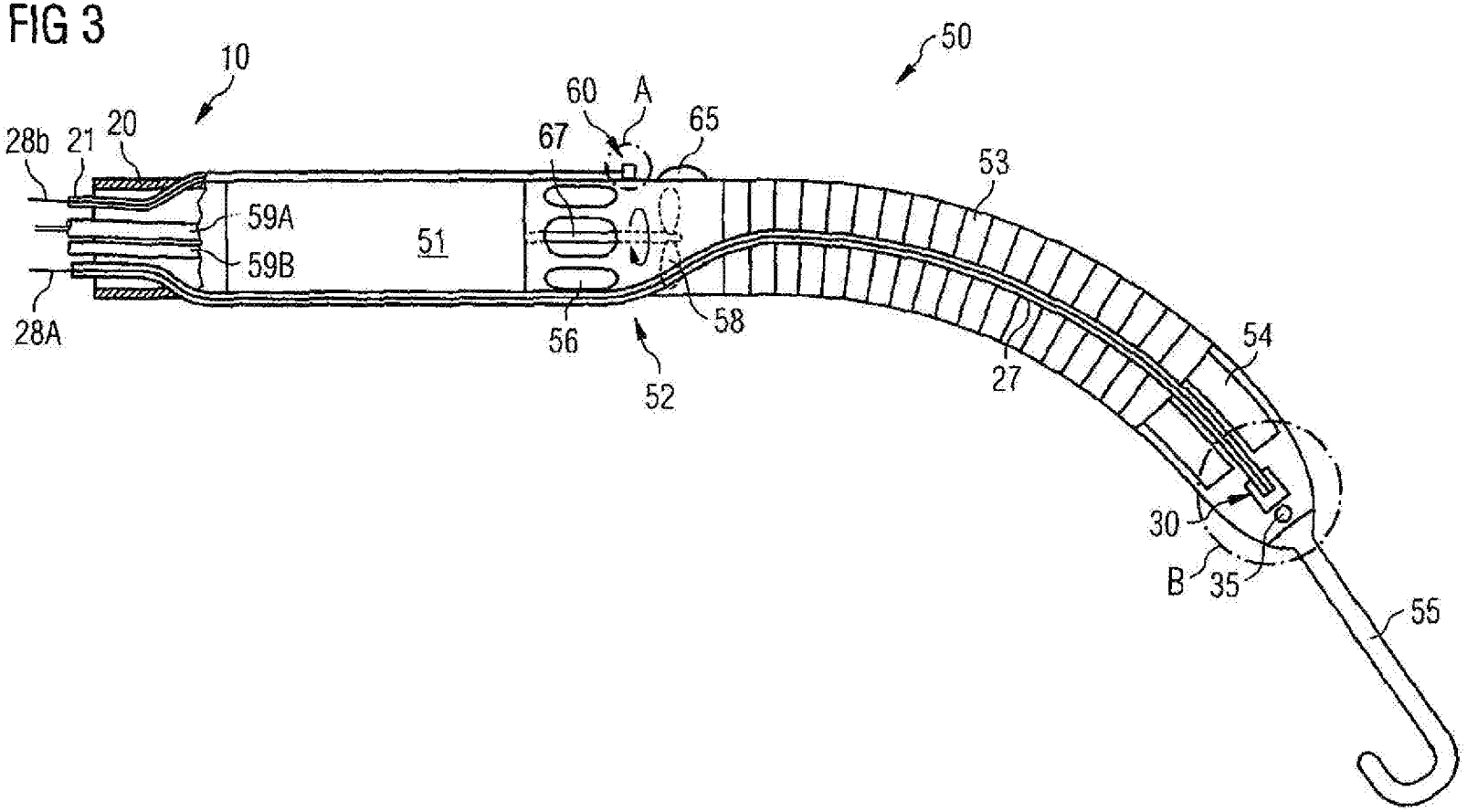
FIG 3
(Amended)

INTRAVASCULAR ROTARY BLOOD PUMP

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED PATENT APPLICATIONS

This application *is an application for reissue of U.S. Pat. No. 9,474,840, which issued from U.S. application Ser. No. 14/396,700, filed on Oct. 23, 2014 which* is a U.S. national phase application claiming the benefit of International Application Serial No. PCT/EP2013/058715, filed on Apr. 26, 2013, which in turn claims the benefit of DE 10 2012 207 053.2, filed on Apr. 27, 2012, the entire disclosures of which are hereby incorporated by reference for all purposes in their entirety as if fully set forth herein.

This invention relates to an intravascular rotary blood pump having one or more pressure sensors for measuring pressures within the patient's vascular system which are significant for operating the blood pump and/or for assessing the state of health of the patient's heart.

WO 2011/039091 A1 describes in connection with a heart support system a pressure-measuring catheter which has a catheter hose and a pressure sensor for measuring the pressure distally of the catheter hose. Concretely, the pressure-measuring catheter has an optical pressure sensor and an elongate tube made of metal or a high-strength plastic, for example PEEK, through which a loosely laid optical fiber of the optical pressure sensor extends. At the anterior (distal) end of the pressure-measuring catheter there is located a sensor head which works on the Fabry-Pérot principle. The sensor head possesses a cavity which is terminated by a thin, pressure-sensitive glass membrane, on the one hand, and into which the end of the optical fiber protrudes, on the other hand. The pressure-sensitive glass membrane is deformed in dependence on the size of the pressure acting on the sensor head. Through the reflection on the glass membrane, the light exiting from the optical fiber is modulatingly reflected and fed into the optical fiber again. At the proximal end of the optical fiber there is located an evaluation unit having an integrated CCD camera, which evaluates the obtained light in the form of an interference pattern. In dependence thereon, a pressure-dependent electrical signal is generated. Altogether this is thus an optoelectronic pressure sensor.

The pressure-measuring catheter is employed in connection with intravascular heart support systems, such as for example an intra-arterial balloon pump (IABP) or an intravascular rotary blood pump, by first advancing the relevant heart support system to the desired place in the patient's vascular system, i.e. for example into the aorta or into a heart chamber, by means of a catheter hose. The pressure-measuring catheter including the tube surrounding the optical fiber is displaceable relative to this catheter hose in its longitudinal direction and is subsequently introduced into the lumen of the catheter hose, advanced through the catheter hose and exits from its end. When the sensor head has reached the intended measurement location, the tube of the pressure-measuring catheter is withdrawn, but can also remain in situ. In connection with a rotary blood pump, it is proposed to push the pressure-measuring catheter far beyond the distal end of the catheter hose and past the pump device of the rotary blood pump, so that it crosses the aortic valve and protrudes with its sensor head into the left ventricle to thereby measure the ventricular pressure.

It would be in principle desirable if the sensor head of the optical pressure sensor was already brought to the proper place with the placement of the rotary blood pump, as is known for example in connection with pressure sensors wherein the pressure is transferred to an extracorporeal pressure-measuring device via a hydrostatic pressure-transfer hose. Thus, there is known for example from US 2003/0187322 A1 a rotary blood pump whose pumping device possesses at the distal end a flow cannula having embedded therein a hydrostatic pressure-transfer hose which extends to the distal end of the flow cannula and is subjected to the blood pressure there.

However, an optical pressure sensor comprising an optical fiber cannot readily be laid along the flow cannula. For the flow cannula, on its way to placement in the heart, is subjected to great bends or flexions which would exert non-negligible tensile and compressive stresses on an optical fiber laid along the flow cannula. Even if the optical fiber was laid freely within a separate pressure-measuring lumen, the frictional forces occurring due to relative motions between the optical fiber and the pressure-measuring lumen could be so great that the optical fiber breaks or tears. This holds in particular for optical fibers made of glass. Such optical fibers are normally covered with a thin plastic coating, such as polyimide (Kapton), which offers some protection from breakage. Nevertheless, the danger of breakage is not ruled out, and it would be great trouble to have to replace the entire blood pump placed in the patient if the optical fiber actually breaks.

The object of the present invention is hence to configure a rotary blood pump having an optical pressure sensor's sensor head fixed to the flow cannula such that the danger of breakage of the optical fiber of the optical pressure sensor is reduced to a great extent.

This object is achieved by an intravascular rotary blood pump having the features of claim 1. Claims dependent thereon state advantageous developments and embodiments of the invention.

Accordingly, an intravascular rotary blood pump, according to a preferred embodiment of the invention, comprises a catheter, a pumping device disposed distally of the catheter and having at its distal end a flexurally flexible flow cannula through which blood is either sucked or discharged by the pumping device during operation of the blood pump, and at least one pressure sensor having at least one optical fiber. According to the invention, the optical fiber is laid along a "neutral fiber" of the flow cannula.

The "neutral fiber" of the flow cannula extends in the longitudinal direction of the flow cannula and is characterized in that it is not, or at least less, preferably considerably less, flexurally flexible than the rest of the flow cannula, so that the flow cannula does not bend, or at least does not bend as easily, along the neutral fiber when the blood pump is guided with the flow cannula in front through the patient's vascular system. By definition, the neutral fiber, upon flexion of the cannula, lies exactly between the compressed and extended regions and ideally undergoes no change of length.

Because the optical fiber extends along the neutral fiber of the flow cannula, i.e. either coincides with a neutral fiber or lies in the same "neutral bending plane" as the neutral fiber, the optical fiber undergoes no compression or extension whatsoever when the rotary blood pump is guided with the flow cannula in front through the patient's vascular system and adapts itself to the different radii of curvature of the vessels.

In the simplest case, the optical fiber can for this purpose be bonded by means of an elastic bonding agent on the inside or outside of the flow cannula along a neutral fiber of the flow cannula. However, for safety's sake it is preferred to dispose the optical fiber in a freely movable manner within a sliding tube laid along the neutral fiber, in order to thereby additionally protect the optical fiber against the risk of breakage due to extensions or compressions.

The neutral fiber of the flow cannula can be realized in different ways. Thus, it is possible for example to impose a neutral fiber, so to speak, by locally strengthening the flow cannula, e.g. by incorporating or applying a flexurally stiff or tensilely and compressively stiff strip along the flow cannula. This is expedient in particular in rotary blood pumps whose flow cannula extends straight in the normal state. Such local strengthening can be obtained for example by a sufficiently rigid lumen or sliding tube in which the optical fiber is laid.

However, the flow cannula frequently has a preset precurvature. Upon navigation of the rotary blood pump through the patient's vascular system, the flow cannula then bends in such a way that this preset curvature becomes stronger and lesser depending on the bending direction. Between the inner radius of curvature and outer radius of curvature of the flow cannula as defined by the precurvature, there is accordingly a neutral fiber, that is, altogether two neutral fibers, namely on both sides of the flow cannula. The precurvature can in turn be preset or stabilized by means of a flexurally stiff strip along the neutral fiber or fibers.

In case the danger of an extension or compression of the optical fiber exists in spite of the optical fiber being laid along the neutral fiber of the flow cannula, it is preferred—as stated—to lay the optical fiber freely movably in a separate sliding tube. Nevertheless, fiber breaks can also occur in this case—as likewise already stated—e.g. because the fiber is subjected to excessive extension or compression within the sliding tube due to high friction. It is hence preferable to choose a sliding material pairing with a low coefficient of friction for the outer surface of the optical fiber and the inner surface of the sliding tube. This may be a metal-metal sliding material pairing, a metal-plastic sliding material pairing or a plastic-plastic material pairing, with the plastic preferably being or at least comprising polytetrafluoroethylene (PTFE).

For this purpose, the optical fiber is accordingly coated with polytetrafluoroethylene on the outer side. Conventional optical fibers, in contrast, are usually coated with polyimide (Kapton). However, the optical fiber can also have an outer metal coating, which can be vapor-deposited for example, in order to form a metal-metal sliding material pairing or metal-plastic sliding material pairing with the inner surface of the sliding tube. For metal regularly has a lower coefficient of friction than conventional plastics.

The sliding tube in which the optical fiber is laid freely movably can be a simple hose, in particular also a stretchable hose, which is possible due to the fact of its being laid along the neutral fiber of the flow cannula. However, a metallic material is preferred for the sliding tube, which might be plastic-coated on the inside, preferably again with polytetrafluoroethylene (PTFE). A metallic sliding tube is compressively and tensilely stable and hence suited for imposing a neutral fiber on the flow cannula. In such rotary blood pumps whose flow cannula already has a preset neutral fiber through precurvature, this neutral fiber is additionally stabilized by the metallic sliding tube.

It is particularly preferred when the sliding tube is formed from a material comprising a shape-memory alloy. The best-known example of such a shape-memory alloy is so-called "nitinol". The special benefit of shape-memory alloys in the present connection is that shape-memory alloys show superelastic behavior. The flow cannula can thereby follow even extreme curvatures without the sliding tube being plastically deformed or the circular cross section being deformed so as to damage the optical waveguide. Instead, the sliding tube bends back into the original shape. Due to this special material property, the lumen can be designed very small with only little clearance for the light guide. Consequently, the cannula, too, can thus still remain thin-walled.

A further advantage of a sliding tube made of shape-memory metal lies in the drastically reduced break sensitivity upon multiple bending load or buckling load. While a "normal" metal tube breaks more easily in this case and thus constitutes a local weak point, thus even increasing the probability of a subsequent fiber break, the tube made of shape-memory metal remains bending-elastic longer and thus continues to reliably prevent fiber break.

It is further preferred when the sliding tube in which the optical fiber is laid freely movably is filled with liquid. This can further reduce the frictional forces between the surface of the optical fiber and the surface of the sliding tube.

The optical fiber employed is preferably a glass fiber, because it is easy to handle and inexpensive. In particular, there are particularly thin glass fibers which do not break even at very narrow bend radii due to their small diameter. This is of special importance in connection with the attachment of the optical fiber to the flow cannula, for it can happen that the flow cannula runs into an obstacle, e.g. the sinus of the aortic valve, and briefly folds 180° when advancing through the blood vessels.

Furthermore, a small diameter of the optical fiber is also advantageous for keeping the cross-sectional dimensions of the blood pump as small as possible. This holds in particular when the optical fiber or the sliding tube containing the optical fiber extends along the flow cannula on the outside. For the greater the diameter of the optical fiber or the diameter of the sliding tube is, the greater the cross-sectional dimensions of the blood pump are, and this can be disadvantageous upon placement of the blood pump and/or upon operation of the blood pump in the patient's vascular system. Hence, it is preferred to provide an optical fiber, in particular an optical fiber comprising a glass fiber, having a diameter of 130 μm or less.

When the sensor head of the pressure sensor or, in general terms, the distal end of the pressure sensor is fixed on the outside of the flow cannula, e.g. on an inflow cage lying at the distal end of the flow cannula, the sensor head is received at least partly in a depression which is provided in the outer surface of the flow cannula. This protects the sensitive sensor head from a collision with a sluice valve or hemostatic valve when the blood pump is being introduced into the patient's vascular system.

However, it may be that the wall thickness of the flow cannula is not sufficient for producing a depression with a depth in which the sensor head can be completely received, so that the distal end of the pressure sensor projects radially beyond the periphery of the flow cannula. In particular in such cases it is advantageous to provide distally before the sensor head a bulge likewise projecting beyond the periphery of the flow cannula, in order to prevent the hemostatic valve or sluice valve from getting caught at the distal end of the pressure sensor when the blood pump is introduced into the patient's vascular system. This bulge can alternatively also be configured such that it is present not only distally before the sensor but also laterally or also proximally. Advantageously, this U- or O-shaped bulge is so configured that the sensor-head contour fits completely into the protective contour, i.e. possesses no edges projecting beyond the protective contour (bulge). This bulge can be for example a bead of bonding agent, which might also only be applied after the sensor head has been fixed in the depression. The bulge can alternatively also be welded or soldered on the flow cannula.

Figure 4A:
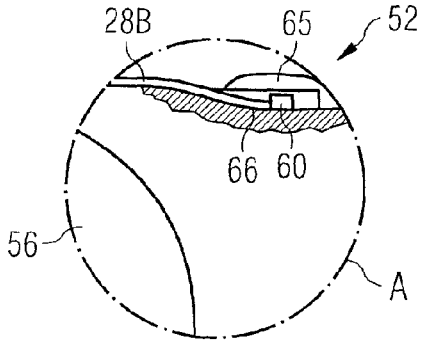
Figure 4B:
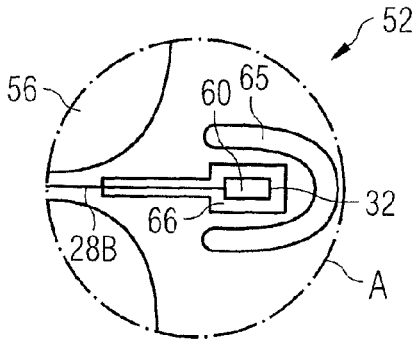
Figure 5A:
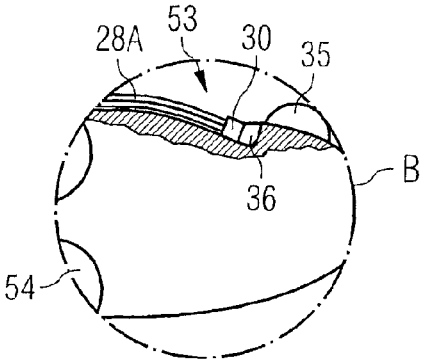
Figure 5B:
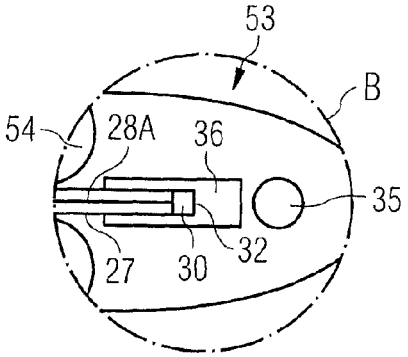
Figure 6:
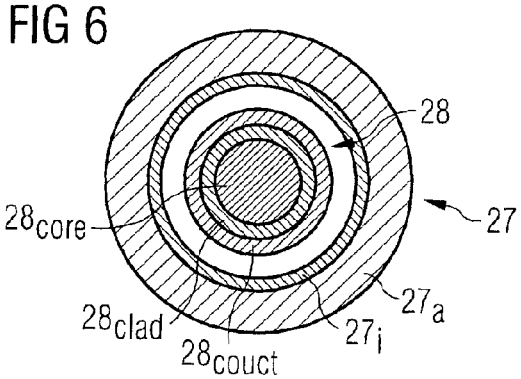

Hereinafter the invention will be explained by way of example with reference to the accompanying drawings. Therein are shown:

FIG. 1 a blood pump laid through the aorta, extending through the aortic valve into the left ventricle and having an integrated pressure sensor, FIG. 2 an optical pressure sensor having an optical fiber, FIG. 3 the pumping device of the blood pump from FIG. 1 in greater detail, FIGS. 4A, 4B the detail A from FIG. 3 in plan view and in side view, FIGS. 5A, 5B the detail B from FIG. 3 in plan view and in side view, and FIG. 6 a cross section through a pressure sensor having an optical fiber guided in a sliding tube.

FIG. 1 shows an intravascular blood pump having a catheter 10 which is introduced into the descending aorta 11 retrograde. The descending aorta is part of the aorta 12 which first ascends from the heart and then descends and has the aortic arch 14. At the beginning of the aorta 12 there is located the aortic valve 15 which connects the left ventricle 16 to the aorta 12 and through which the intravascular blood pump extends. The intravascular blood pump comprises in addition to the catheter 10 a rotary pumping device 50 fastened at the distal end of the catheter hose 20 and having a motor section 51 and a pump section 52 disposed at an axial distance therefrom, as well as a flow cannula 53 protruding in the distal direction from the inflow end of the pump section 52 and having a suction inlet 54 located at its end. Distally of the suction inlet 54 there is provided a soft-flexible tip 55, which can be configured for example as a "pigtail" or in a J shape. Through the catheter hose 20 there extend different lines and devices which are important for operating the pumping device 50. Of these, FIG. 1 only shows two optical fibers 28A, 28B which are attached at their proximal end to an evaluation device 100. These optical fibers 28A, 28B are respectively part of an optical pressure sensor whose sensor heads 30 and 60 are located on the outside on the housing of the pump section 52, on the one hand, and on the outside in the vicinity of the suction inlet 54, on the other hand. The pressure transmitted by the sensor heads 30 and 60 is converted into electrical signals in the evaluation device 100 and displayed e.g. on a display screen 101.

The measurement of both the aortic pressure by means of the sensor head 60 and the ventricular pressure by means of the sensor head 30 makes possible, in addition to the actual pressure signal, e.g. a contractility measurement by which the recovery of the heart is measured, as well as the establishment of the pressure difference which is used for computing the flow of the pumping device 50.

The principle of electro-optical pressure measurement will be explained more closely hereinafter with reference to FIG. 2. FIG. 2 shows a pressure-measuring catheter 26 having a lumen or sliding tube 27 in which an optical fiber 28A (which might also be a plurality of optical fibers or the optical fiber 28B) is freely movable. The sliding tube 27 can consist of a polymer, in particular polyurethane, or preferably of nitinol or another shape-memory alloy, exit from the catheter hose 20 at an exit point 57 (cf. FIG. 1), and be laid along the flexible flow cannula 53 e.g. on the outside. Within the catheter hose 20 the separate sliding tube 27 can be omitted. At the distal end 34 of the optical fiber 28A the pressure-measuring catheter has a sensor head 30 having a head housing 31 which contains a thin glass membrane 32 which terminates a cavity 33. The glass membrane 32 is pressure-sensitive and is deformed in dependence on the size of a pressure acting on the sensor head 30. Through the reflection on the membrane the light exiting from the optical fiber 28A is reflected modulatingly and coupled back into the optical fiber. The coupling in can be effected either directly into the form 28A or indirectly via a bottom 37 terminating the cavity 33 in a vacuum-tight manner. Advantageously, the bottom 37 is an integral part of the head housing 31. Thus, the specification of the pressure in the cavity 33 can be effected independently of the mounting of the optical fiber 28A. At the proximal end of the optical fiber 28A, i.e. in the evaluation device 100, there is located a digital camera, such as e.g. a CCD camera or a CMOS, which evaluates the incoming light in the form of an interference pattern. In dependence thereon, a pressure-dependent electrical signal is generated. The evaluation of the optical image or optical pattern delivered by the camera and the computation of the pressure are effected through the evaluation unit 100. The latter passes the already linearized pressure values to the control means, which also controls the power supply to the motor-operated pumping device 50 in dependence on the effected evaluation of the pressure signal.

Instead of the optical pressure sensor described with reference to FIG. 2, which works on the Fabry-Pérot principle, other optical pressure sensors with one or more optical fibers can also be employed.

The pumping device 50 from FIG. 1 is represented in further detail in FIG. 3. One can see a drive shaft [57] *67* protruding from the motor section 51 into the pump section 52, which drives an impeller 58 by means of which, during operation of the blood pump, blood is sucked through the blood pass-through openings 54 at the distal end of the flexible flow cannula 53 and discharged proximally of the impeller 58 through the blood-flow pass-through openings 56. The pumping device 50 can also pump in the reverse direction when it is adapted accordingly. Leading through the catheter hose 20 of the catheter 10 to the pumping device 50 are the above-mentioned optical fibers 28A, 28B, on the one hand, and a power-supply line 59A for the motor section 51 and a purge-fluid line 59B.

The sensor head 60 of the first pressure sensor is fixed on the outside of the pump housing of the pump section 52. The appurtenant optical fiber 28B is guided in a thin plastic hose 21 over a short distance of for example 5 cm within the catheter hose 20, in order to ensure that the optical fiber 28B does not break upon strong curvatures of the catheter 10 in this region of the catheter hose 20. Outside the pumping device 50 the optical fiber 28B is laid freely and only bonded to the outer wall of the pumping device 50 by means of bonding agent. This minimizes the outer cross-sectional dimensions of the pumping device 50. The bonding of the optical fiber 28B is possible because the pumping device 50 is rigid in this region and the optical fiber 28B hence does not have to be movable relative to the pumping device 50.

In contrast, the optical fiber 28A leading to the sensor head 30 of the second pressure sensor is laid freely in a hose or tubelet, preferably a nitinol tubelet, along the total periphery of the pumping device 50, so that it can shift relative to the pumping device 50 within this hose or tubelet upon changes of bend of the flow cannula 53. The hose or tubelet thus forms the sliding tube 27 for the optical fiber 28A and extends along a neutral fiber of the flow cannula 53 on the outer surface of the flow cannula. It is likewise possible to lay the sliding tube 27 inside the flow cannula 53, in particular when a pressure inside the flow cannula 53 is to be measured, or to integrate it into the walling of the flow cannula 53.

The neutral fiber of the flow cannula 53, in the exemplary embodiment represented in FIG. 3, results from the flow cannula possessing a precurvature which facilitates the laying of the blood pump in the patient's vascular system. Due to this precurvature, the flow cannula 53 has an inner radius of curvature and an outer radius of curvature between which, substantially in the middle, a neutral bending plane extends. The flow cannula 53 possesses neutral fibers where this central bending plane intersects the flow cannula. The neutral fiber or neutral plane of the flow cannula 53 as preset by the precurvature is strengthened by the sliding tube 27 laid there. However, a neutral fiber of the flow cannula as intended by the present invention is also understood to include all other lines extending within the neutral plane, since no line or "fiber" extending within this plane is subjected to pressure loads or tensile loads when the precurvature of the flow cannula 53 is strengthened or lessened on its way through the patient's vascular system. The strengthening of the neutral fiber by the sliding tube 27 can moreover be of special advantage, since it prevents or at least lessens a bend of the cannula perpendicular to the sheet plane. This anisotropy can make it easier for the user to advance the cannula through the curved vascular system.

As explained at the outset, the optical fiber 28A can also be laid and fixed along a neutral fiber of the flow cannula 53 directly without an additional sliding tube 27. Freely laying the optical fiber 28A within the sliding tube 27 laid along the neutral fiber serves only to give the optical fiber 28A additional resistance to breakage.

The hose and/or tubelet of the sliding tube 27 in which the optical fibers 28A, 28B are laid can extend shortly into the catheter hose 20, but can also extend completely through the catheter hose 20 and end in a corresponding plug at the end of the line for insertion of the relevant pressure sensor into a connection of the evaluation device 100.

Distally before and/or beside and/or behind the sensor heads 30 and 60 there is respectively provided a bulge 35, 65 which protects the sensor heads 30 and 60 from damage upon introduction of the blood pump through a hemostatic valve or sluice valve. Furthermore, the sensor heads 30 and 60 are respectively set in a depression 36, 66 of the pumping device 50. This is not represented in FIG. 3 and will be explained hereinafter with reference to FIGS. 4A, 4B and 5A, 5B.

FIG. 4A shows the detail A from FIG. 3 in greater detail and partly in cross section. FIG. 4B basically shows the same detail A but in plan view from above. Accordingly, the sensor head 60 is received in a countersunk manner in a depression 66 provided on the outer surface of the pump section 52, the depression 66 being surrounded by a horseshoe- or U-shaped bulge 65. The bulge could also be closed to form an O shape. It is bonded on or welded on, but can also form an integral part of the pump section 52. The optical fiber 28B is bonded on the surface and extends along a bar between two blood-flow pass-through openings 56.

In a similar manner (FIGS. 5A and 5B), the sensor head 30 of the second pressure sensor is also received in a countersunk manner in a depression 36 on the outer surface at the distal end of the flow cannula 53. Here, too, the nitinol tubelet 27 with the optical fiber 28A laid therein extends through over a bar between two blood-flow pass-through openings 54. A point-shaped bulge 35 distally directly before the depression 36 protects the sensor head 30 from collision damage upon introduction of the blood pump. The bulge 35, too, can alternatively be configured in a U shape or O shape and in particular be bonded on, welded on or an integral part of the flow cannula 53.

The sensor head 30 can alternatively extend together with the sliding tube 27 up to an arbitrary place on the soft-flexible tip 55 and be protected mechanically there e.g. by the walling of the soft-flexible tip 55. Bending-induced pressure artifacts are low, since the sensor membrane is disposed orthogonally to the walling. Only the bonded connection between the optical waveguide 34 and the sensor head must be protected against bending. This can be effected through the tubelet 27 or an additional stiffening in the region of the bonding.

The optical fiber 28B as well as the optical fiber 28A are preferably glass fibers, which are usually polymer-coated. Optical fibers made of plastic are likewise employable. However, optical fibers made of glass can be manufactured especially thin, which is favorable—in particular in combination with the additional sliding tube 27—for minimizing the total cross section of the pumping device 50. It is thus advantageous to employ optical fibers with a glass core which do not exceed a total diameter of 130 μm. It is true that such thin optical fibers are especially in danger of breaking when they are subjected to tensile or compressive forces. However, this risk is reduced to a great extent by disposing the optical fiber along the neutral fiber of the flow cannula 53. The sliding tube 27 can then possess an inner diameter of only 150 μm. The outer diameter then lies slightly thereabove, for example at 220 μm, so that the total cross section of the pumping device 50 is not significantly increased. For it is to be taken into consideration that the sliding tube 27 must always be laid outside the pumping device 50 at least in the region of the pump section 52. Tubelets made of the shape-memory alloy, nitinol, are commercially available with the above-mentioned inner and outer diameters. However, it is also possible to employ sliding tubes, in particular nitinol tubelets, with greater diameters, for example an inner diameter of 230 μm and an outer diameter of 330 μm. The optical fiber 28A can then also have an accordingly greater diameter.

FIG. 6 shows a cross section through a sliding tube 27 with an optical fiber 28 laid therein, which comprises a glass-fiber core $\mathbf{28}_{core}$, a so-called cladding $\mathbf{28}_{clad}$ likewise made of glass and an outer polymer coating $\mathbf{28}_{coat}$. The different refractive indices of the optical-fiber core $\mathbf{28}_{core}$ and of the optical-fiber cladding $\mathbf{28}_{clad}$ ensure that light coupled into the optical-fiber core is transmitted along the optical fiber 28 virtually losslessly. The outer coating $\mathbf{28}_{coat}$ serves to protect the optical fiber 28 against breakage. While the coating $\mathbf{28}_{coat}$ is usually a polyimide coating, it is advantageous within the scope of the present invention to provide a coating $\mathbf{28}_{coat}$ as low in friction as possible, in particular made of polytetrafluoroethylene (PTFE). The outer coating $\mathbf{28}_{coat}$ can also be a metallic coating. The glass-fiber core $\mathbf{28}_{core}$ can possess a diameter of e.g. 62.5 μm. The reflective layer could then increase the diameter to 80 μm. The coating $\mathbf{28}_{coat}$ can possess a thickness of 10 μm. The diameter of the optical fiber 28 preferably amounts altogether to approx. 100 μm or less.

There is a distinction between normal optical fibers and graded-index fibers. In graded-index fibers the glass-fiber cladding $28_{clad}$ is formed by a plurality of superjacent glass layers with different refractive indices. The employment of graded-index fibers is preferred in connection with the present invention because they are more bendable and more lossless than simple glass fibers.

The sliding tube 27 consists for its part of an outer casing 27a, with an inner-side coating 27i. The outer casing 27a substantially defines the bending and extension properties of the sliding tube 27, while the inside coating 27i is essential for reducing the frictional forces acting between the sliding tube 27 and the optical fiber 28. The inside coating 27i is hence preferably a metallic coating or again a low-friction polymer coating, in particular made of polytetrafluoroethylene.

The sliding tube 27 can additionally be filled with a liquid in order to minimize frictional forces that occur.

The invention claimed is:

1. An intravascular rotary blood pump, comprising a catheter (10), a pumping device (50) disposed distally of the catheter (10) and having at its distal end a flexurally flexible flow cannula (53) through which blood is either sucked or discharged by the pumping device (50) during operation of the blood pump, and at least one pressure sensor (27, 28A, 30) having at least one optical fiber (28A), characterized in that the optical fiber (28A) is laid along a neutral fiber of the flow cannula (53).

2. The blood pump according to claim 1, wherein the neutral fiber is preset by a precurvature of the flow cannula (53) and accordingly lies between an inner radius of curvature and outer radius of curvature of the flow cannula as defined by the precurvature.

3. The blood pump according to claim 1, wherein the optical fiber (28A) is bonded along the neutral fiber.

4. The blood pump according to claim 1, wherein the optical fiber (28A) is laid freely movably in a sliding tube (27) along the neutral fiber.

5. The blood pump according to claim 4, wherein the sliding tube (27) extends along the flow cannula (53) on the outside.

6. The blood pump according to claim 4, wherein an outer surface of the optical fiber (28A) and an inner surface of the sliding tube (27) form a sliding material pairing of metal-metal, metal-plastic or plastic-plastic.

7. The blood pump according to claim 6, wherein the plastic comprises polytetrafluoroethylene (PTFE).

8. The blood pump according to claim 4, wherein the sliding tube (27) is formed from a material comprising a shape-memory alloy.

9. The blood pump according to claim 4, wherein the sliding tube (27) is plastic-coated on the inside.

10. The blood pump according to claim 4, wherein the optical fiber (28A) has an outer metal coating ($28_{coat}$).

11. The blood pump according to claim 4, wherein the optical fiber (28A) has an outer plastic coating ($28_{coat}$) made of polytetrafluoroethylene (PTFE).

12. The blood pump according to claim 4, wherein the sliding tube (27) is filled with liquid.

13. The blood pump according to claim 1, wherein the optical fiber (28A) comprises a glass fiber ($28_{core}$, $28_{clad}$, $28_{coat}$).

14. The blood pump according to claim 1, wherein the optical fiber (28A) possesses a diameter of 130 μm or less.

15. The blood pump according to claim 1, wherein the flow cannula (53) has an outer surface in which there is configured a depression (36) in which a distal end (30) of the pressure sensor is at least partly disposed.

16. The blood pump according to claim 1, wherein the flexurally flexible flow cannula (53) has a soft-flexible tip (55) and wherein a distal end (30) of the pressure sensor is at least partly disposed in the soft-flexible tip (55).

17. The blood pump according to claim 1, wherein a distal end (30) of the pressure sensor projects radially beyond the periphery of the flow cannula (53), and wherein there is provided on the flow cannula (53) distally before the distal end (30) of the pressure sensor a bulge (35) likewise projecting beyond the periphery of the flow cannula (53).

*18. An intravascular rotary blood pump, comprising:*

*a catheter (10),*

*a pumping device (50) disposed distally of the catheter (10) and having at its distal end a flexurally flexible flow cannula (53) through which blood is either sucked or discharged by the pumping device (50) during operation of the blood pump, and*

*at least one pressure sensor (27, 28A, 30) having at least one optical fiber (28A) laid moveably in a tube (27), the tube (27) is fixed along a neutral fiber of the flow cannula (53) selected to prevent breakage of the fiber (28A) during bending of the flow cannula (53) while the blood pump is guided through a vascular system of a patient, the tube (27) strengthening the neutral fiber of the flow cannula (53).*

*19. The blood pump according to claim 18, wherein the tube (27) extends through walling of the flow cannula (53).*

*20. The blood pump according to claim 18, wherein the tube (27) extends along an outer surface of the flow cannula (53).*

*21. The blood pump according to claim 18, wherein the optical fiber (28A) is configured to undergo substantially no extension while the blood pump is guided through the vascular system of the patient.*

*22. The blood pump according to claim 18, wherein the optical fiber (28A) is configured to undergo substantially no compression while the blood pump is guided through the vascular system of the patient.*

*23. An intravascular rotary blood pump, comprising:*

*a catheter (10),*

*a pumping device (50) disposed distally of the catheter (10) and having at its distal end a flexurally flexible flow cannula (53) through which blood is either sucked or discharged by the pumping device (50) during operation of the blood pump, and*

*at least one pressure sensor (27, 28A, 30) having at least one optical fiber (28A) laid along a portion of the flow cannula (53) and extending in a longitudinal direction of the flow cannula (53), wherein the portion of the flexurally flexible flow cannula (53) is less flexurally flexible than the rest of the flexurally flexible flow cannula (53).*

*24. The blood pump according to claim 23, wherein the optical fiber (28A) extends through walling of the flow cannula (53).*

*25. The blood pump according to claim 23, wherein the optical fiber (28A) extends along an outer surface of the flow cannula (53).*

*26. The blood pump according to claim 23, wherein the optical fiber (28A) is configured to undergo substantially no extension while the blood pump is guided through the vascular system of the patient.*

*27. The blood pump according to claim 23, wherein the optical fiber (28A) is configured to undergo substantially no*

*compression while the blood pump is guided through the vascular system of the patient.*

* * * * *